United States Patent [19]

Nishimura et al.

[11] Patent Number: 5,292,711

[45] Date of Patent: Mar. 8, 1994

[54] THERMOSENSITIVE RECORDING MATERIAL

[75] Inventors: Masaki Nishimura, Tokyo; Kunitaka Toyofuku, Sakura; Yoshiyuki Takahashi, Kawasaki, all of Japan

[73] Assignee: Oji Paper Co., Ltd., Tokyo, Japan

[21] Appl. No.: 878,389

[22] Filed: May 5, 1992

[30] Foreign Application Priority Data

May 10, 1991 [JP] Japan .................. 3-105818
Oct. 25, 1991 [JP] Japan .................. 3-279965

[51] Int. Cl.$^5$ ............................. B41M 5/32
[52] U.S. Cl. .................. 503/209; 503/216; 503/225
[58] Field of Search ............ 503/207, 209, 214, 216, 503/225

[56] References Cited

U.S. PATENT DOCUMENTS 3,859,112  1/1975  Kohmura et al. ............ 106/308
3,936,309  2/1976  Kohmura et al. ............ 106/21

FOREIGN PATENT DOCUMENTS 0196164 10/1986 European Pat. Off. .
0382523 8/1990 European Pat. Off. .
2327135 12/1973 Fed. Rep. of Germany .
60-219088 11/1985 Japan .
62-164579 7/1987 Japan .

OTHER PUBLICATIONS

World Patents Index Latest, Week 8525, Derwent Publications Ltd., London, GB, JP-A-60 083 884, May 13, 1985 (Abstract).
World Patents Index Latest, Week 8550, Derwent Publications Ltd., London, GB, JP-A-60 220 787, Nov. 5, 1985 (Abstract).
World Patents Index Latest, Week 9101, Derwent Publications Ltd., London, GB, JP-A-2 281 991, Nov. 19, 1990 (Abstract).
W. Gerhartz et al, *Ullmann's Encyclopedia of Industrial Chemistry*, 1987, 5th edition, vol. A9: "Epoxy Resins", pp. 554-556.

Primary Examiner—Pamela R. Schwartz
Attorney, Agent, or Firm—Armstrong, Westerman, Hattori, McLeland & Naughton

[57] ABSTRACT

A thermosensitive recording material, capable of providing colored images having a high resistance to oily substances and plasticizers and an excellent storage persistency for a long time, comprises a thermosensitive colored image-forming layer formed on a sheet substrate and comprising a colorless dye precursor, a color developing agent, a colored image-stabilizing agent comprising an aziridinyl compound and/or an epoxy compound, and an additional colored image-stabilizing agent comprising a primary or secondary amine compound and/or a carboxylic compound having a carboxyl group or —CO—O—CO— group; the color developing agent preferably comprising a compound of the formula (I):

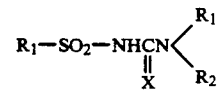

wherein X is an O or S atom, $R_1$ is an unsubstituted aromatic group, or a substituted phenyl group having a lower alkyl or a halogen atom, and $R_2$ and $R_3$ are respectively a hydrogen atom, or alkyl group, aryl groups, substituted alkyl group with an aryloxy group, or a substituted aromatic group having an alkyl, aryl, aralkyl, alkyloxy, alkyloxycarbonyl, aryloxycarbonyl, aralkyloxycarbonyl or arylsulfonyl group or a halogen atom.

8 Claims, No Drawings

THERMOSENSITIVE RECORDING MATERIAL

BACKGROUND OF THE INVENTION

1. Field of the Invention

The present invention relates to a thermosensitive recording material on which colored images are formed by heating. More particularly, the present invention relates to a thermosensitive recording material capable of forming thereon colored images having a high persistency for a record storage thereof for a long time.

The thermosensitive record material of the present invention is able to record thereon colored images exhibiting an excellent resistance to moisture, heat, oily and fatty substances, and plasticizers, and thus has a superior stability when stored for a long time, and therefore is useful as colored image-recording sheets, sheets for use in facsimiles, word processors, CRT image printers and cash dispensers, as passenger tickets, commuter's passes, labels such as POS labels, cards such as prepaid cards, and as transit passes.

2. Description of the Related Arts

It is known that a conventional thermosensitive recording material comprises a supporting substrate, for example, a paper sheet, synthetic paper sheet, or plastic resin film, and a thermosensitive colored image-forming layer formed on a surface of the supporting substrate and comprising an electron-donative dye precursor, for example, a leuco basic dye, an electron-acceptive color-developing agent consisting of an organic acid substance, for example, a phenol compound, and a binder. When the thermosensitive colored image-forming layer is heated, colored images are recorded thereon by a reaction of the dye precursor with the color-developing agent.

This type of thermosensitive recording material is disclosed in Japanese Examined Patent Publication Nos. 43-4,160 and 45-14,039 and Japanese Unexamined Patent Publication No. 48-27,736, and is widely employed in practice.

Namely, the thermosensitive recording material is advantageous in that colored images can be easily formed only by heating, and the recording apparatus can be made relatively compact and small size, has a low cost, and is easily maintained, and thus is useful as an information-recording material for various outputs or printers used with, for example, computers, facsimile machines, automatic ticket-vending machines, scientific measurement recorders, and CRT medical measurement recorders.

Nevertheless, the conventional dye-forming type thermosensitive recording materials in which the thermosensitive colored image-forming layer comprises a conventional color-developing agent together with the dye precursor and the binder, is disadvantageous in that the reaction of the dye precursor with the color-developing agent is reversible, and thus the resultant colored images fade with a lapse of time. This fading of the colored images is accelerated by exposure to light, high temperatures and high humidity, and promoted by contact with an oily or fatty substance or a plasticizer, and the colored images fade to an extent such that the faded images cannot be recognized.

With the expansion of the scope of application of the thermosensitive recording material, a possibility of contact of the thermosensitive recording materials with cosmetic creams, oils or plastic polymer articles containing plasticizer, or of exposure to hard conditions, for example, high temperature and high humidity, is increased. For example, when colored images formed in a thermosensitive recording material containing a conventional color developing agent comprising 2,2-bis(4-hydroxyphenyl)propane, i.e., bisphenol A, or benzyl p-hydroxybenzoate (disclosed in Japanese Unexamined Patent Publication No. 52-140,483) is exposed to a high temperature and high humidity condition, the color density of the colored images is lowered. Also, when brought into contact with the plasticizer or the oil or fat substance, the colored images are faded and become unreadable.

Many attempts have been made to inhibit the color-fading of the colored images formed on the conventional thermosensitive colored image-forming layer containing a substantially colorless dye precursor comprising a lactone ring compound.

For example, Japanese Unexamined Patent Publication Nos. 60-78,782, 59-167,292, 59-114,096 and 59-93,387 disclose a thermosensitive colored image-forming layer containing a phenolic antioxidant.

Japanese Unexamined Patent Publication No. 56-146,796 discloses a protective layer formed from a hydrophobic polymeric compound emulsion on a thermosensitive colored image-forming layer.

Japanese Unexamined Patent Publication No. 58-199,189 discloses an intermediate layer formed from a water-soluble polymeric compound solution or a hydrophobic polymeric compound emulsion on a thermosensitive colored image-forming layer, and a surface layer formed from a solution of a hydrophobic polymer in a solvent on the intermediate layer.

Japanese Unexamined Patent Publication No. 62-164,579 and No. 60-219,088 discloses a thermosensitive colored image-forming layer containing an additive consisting of an epoxy compound and/or an aziridine compound.

In the thermosensitive colored image-forming layer containing the phenolic antioxidant, the resultant colored images exhibit a higher resistance to heat and moisture and a longer persistency in the ambient atmosphere than those of a conventional colored image-forming layer free from the phenolic antioxidant, but the improvement in the storage stability of the resultant colored images is still not satisfactory. Also, the phenolic antioxidant does not effectively enhance the resistance of the colored images to the oily or fatty substances, for example, salad oil, and plasticizers, for example, dioctyl phthalate. The resistance of the colored images to oily or fatty substance or plasticizer is determined in such a manner that an oily or fatty substance, for example, a salad oil, or a plasticizer, is brought into contact with colored images, the colored images are left in contact with the oily or fatty substance or the plasticizer for a predetermined time, and then a retention of the color density of the tested colored images is measured in comparison with an initial color density thereof.

When the protective layer or the intermediate and surface layers are formed on the thermosensitive colored image-forming layer, the resultant colored images have a satisfactory resistance to the oily and fatty substances and to the plasticizers, and exhibit a significantly enhanced storage persistency when the salad oil or the dioctyl phthalate is brought into contact with the colored image-forming surface of the recording material. Nevertheless, when the salad oil or the dioctyl phthalate is brought into contact with an edge face of the recording material, it penetrates into the inside of the recording material and causes the colored images to be substantially completely faded. Therefore, the provision of the protecting layer or the intermediate and surface layer cannot completely eliminate the undesirable color-fading of the images.

The addition of the epoxy compound and/or aziridinyl compound to the colored image-forming layer is unsatisfactory in that it takes a long time to satisfactorily stabilize the colored images formed on the colored image-forming layer by a heat-recording operation, and therefore, if an oily or fatty substance, for example, salad oil, or a plasticizer, for example, dioctyl phthalate, is brought into contact with the colored image-forming layer immediately after the heat-recording operation, the resultant colored images are faded to a great extent.

SUMMARY OF THE INVENTION

An object of the present invention is to provide a thermosensitive recording material allowing colored images formed thereon to exhibit an excellent resistance to oily and fatty substances and to plasticizers even immediately after the formation of the colored images, and thus have a superior persistency over a long time.

Another object of the present invention is to provide a thermosensitive recording material useful for thermorecording type tickets of automatic ticket machine, for commuter's passes, and for coupon tickets, which must have a high persistency, in terms of the quality of the colored images recorded thereon, for a long time, for label sheets in a POS bar code price-indicating system, to be attached to a surface of a polyvinyl chloride film containing a plasticizer and wrapping fresh food or meat containing an oily or fatty substance, which label sheets are unavoidably brought into contact with the plasticizer and/or oily or fatty substance, for facsimile recording sheets and word processor recording sheets which must have a high persistency, and for CRT image printing sheets.

The above-mentioned objects can be attained by the thermosensitive recording material of the present invention, which comprises a sheet substrate, and a thermosensitive colored image-forming layer formed on a surface of the sheet substrate and comprising a substantially colorless dye precursor, a color developing agent reactive with the dye precursor upon heating to thereby develop a color, a colored image-stabilizing agent comprising at least one member selected from the group consisting of aromatic aziridinyl compounds having at least one aziridinyl group and aromatic epoxy compounds having at least one epoxy group, and a binder, the thermosensitive colored image-forming layer further containing an additional colored-image-stabilizing agent comprising a member selected from the group consisting of amino compounds having at least one member selected from the group consisting of primary and secondary amine groups, mixtures of at least two of the amino compounds, carboxylic compounds having at least one member selected from the group consisting of carboxyl group and a group of the formula of —CO—O—CO—, and mixtures of at least two of the carboxyl compounds.

In the thermosensitive recording material of the present invention, the color developing agent preferably comprises at least compound of the formula (I):

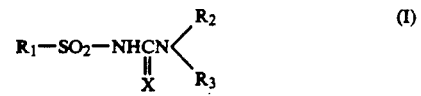

wherein X represents a member selected from the group consisting of oxygen and sulfur atoms, $R_1$ represents a member selected from the group consisting of unsubstituted aromatic cyclic hydrocarbon groups and substituted phenyl group having at least one member selected from the group consisting of lower alkyl groups and halogen atoms, and $R_2$ and $R_3$ respectively and independently from each other represent a member selected from the group consisting of a hydrogen atom, alkyl groups, aryl groups, aralkyl groups, substituted alkyl groups having an aryloxy group, unsubstituted aromatic cyclic hydrocarbon groups, and substituted aromatic cyclic hydrocarbon groups having at least one member selected from the group consisting of alkyl groups, aryl groups, aralkyl groups, alkyloxy groups, alkyloxycarbonyl groups, aryloxycarbonyl groups, aralkyloxycarbonyl groups, arylsulfonyl groups and halogen atoms.

DESCRIPTION OF THE PREFERRED EMBODIMENTS

In this specification, the epoxy group is of the formula:

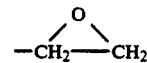

which will be represented hereafter by an abbreviated formula:

In the thermosensitive recording material of the present invention, a thermosensitive colored image-forming layer is arranged on a surface of a sheet substrate, and comprises a substantially colorless dye precursor, a color developing agent reactive with the dye precursor upon heating to thereby develop a color, a specific colored image-stabilizing agent, a specific additional colored image-stabilizing agent and a binder.

In the present invention, the specific colored image-stabilizing agent must be employed in combination with the specific additional colored image-stabilizing agent, to enhance the resistances of the colored images to the oily and fatty substances and to the plasticizers contained in a thermoplastic resin articles.

The color image-stabilizing agent usable for the present invention comprises at least one member selected from the group consisting of aromatic aziridinyl compounds having at least one azirinyl group, and aromatic epoxy compounds having at least one epoxy group.

The aromatic aziridinyl compound usable for the colored image-stabilizing agent is preferably selected from the group consisting of 2,4-bis(1-aziridinylcarbonylamino)toluene, bis[4-(1-aziridinylcarbonylamino)-phenyl]methane, bis[3-chloro-4-(1-aziridinylcarbonylamino)phenyl]methane, 2,2-bis[4-(1-aziridinylcarbonyloxy)phenyl]propane, 1,4-bis(1-aziridinylcarbonyloxy)benzene and 1,4-bis(1-aziridinyl-carbonyl)-benzene.

The aromatic epoxy compound usable for the colored image-stabilizing agent is preferably selected from the group consisting of the compounds of the formulae 1) to 15):
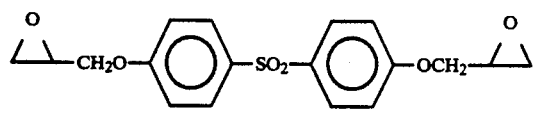 1)
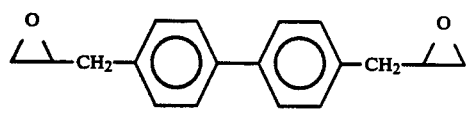 2)
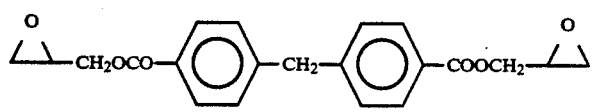 3)
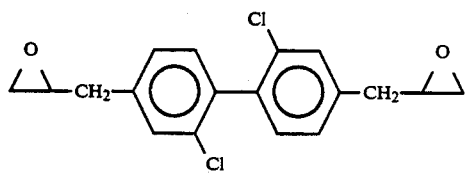 4)
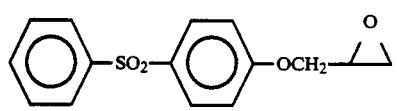 5)
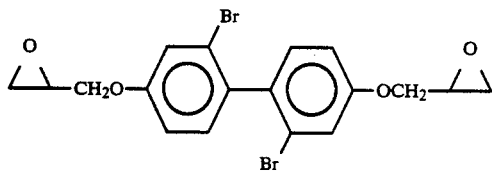 6)
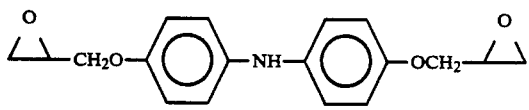 7)
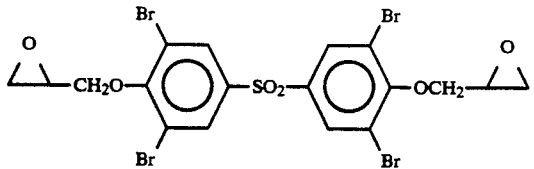 8)
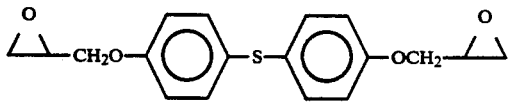 9)
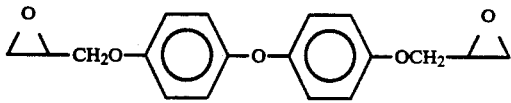 10)
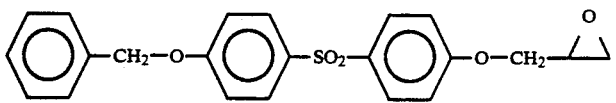 11)

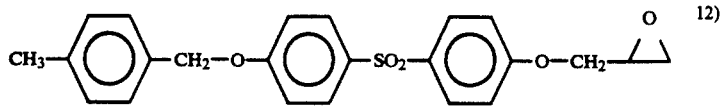

12)

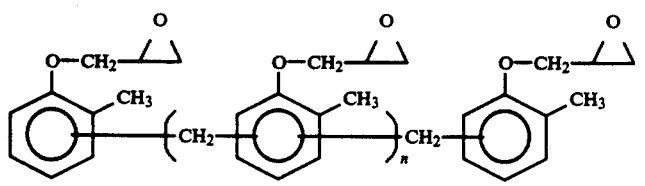

13)

in which formula 13, n represents an integer of 1 to 10,

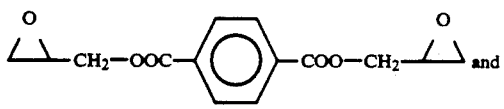

14)

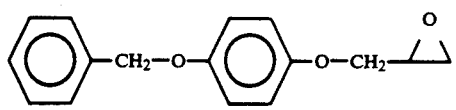

15)

The specific additional colored image-stabilizing agent comprises a member selected from the group consisting of amino compounds having at least one member selected from the group consisting of primary and secondary amine groups, mixtures of at least two of the amino compounds, carboxylic compounds having at least one member selected from the group consisting of a carboxyl group and a —CO—O—CO— group, and mixtures of at least two of the carboxyl compounds. Namely, the additional colored image-stabilizing agent comprises one of or a mixture of two or more of the amino compounds or one of or a mixture of two or more of the carboxyl compounds.

Preferably, the amino compound having at least one member selected from the group consisting of primary amine group (—NH$_2$) and secondary amine group (—NH—), and usable for the additional colored image-stabilizing agent, is selected from the group consisting of the compounds of the formulae 16) to 25):

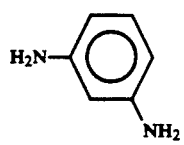

16)

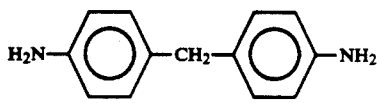

17)

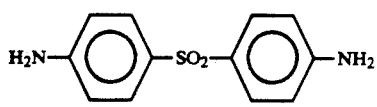

18)

19)

20)

21)

22)

23)

24)

25)

The carboxyl compound having at least one member selected from the group consisting of a carboxyl group (—COOH) and a —CO—O—CO— group, and usable for the additional colored image-stabilizing agent is preferably selected from the group consisting of the compounds of the formulae 26) to 37):

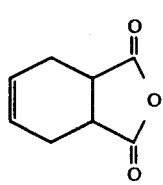

26)

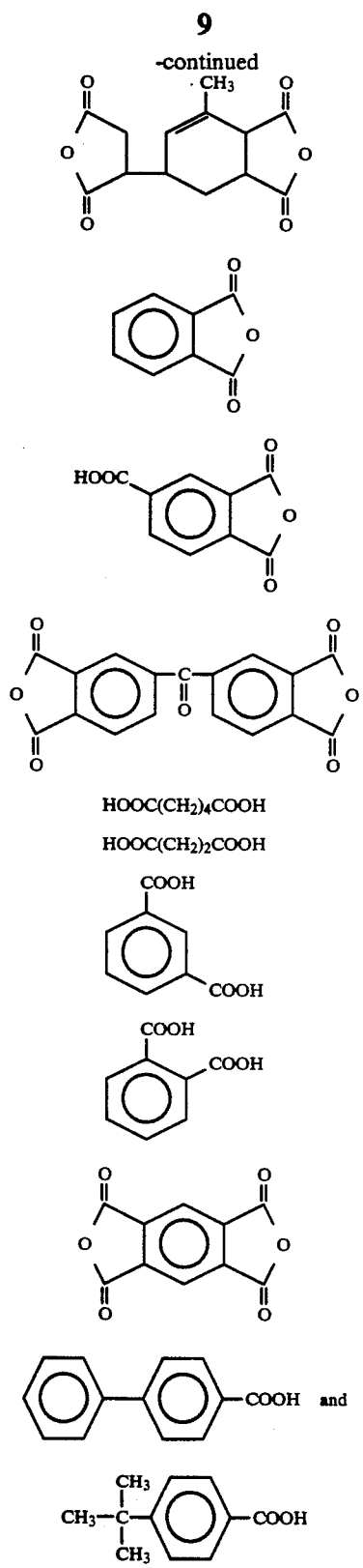

The reasons for which the combination of the specific colored image-stabilizing agent with the specific additional colored image-stabilizing agent effectively enhance the resistances of the colored images to the oily and fatty substances and the plasticizers have not yet been completely clarified, but nevertheless, it is assumed that, when colored images are formed from the reaction of the dye precursor and the color developing agent upon heating, the amino compound or the carboxylic compound of the additional colored image-stabilizing agent reacts with the aziridinyl compounds and/or the epoxy compound of the colored image-stabilizing agent to form a certain compound which is insoluble in the oily and fatty substances or in the plasticizer, and which protects the colored images.

In the thermosensitive recording material of the present invention, the color developing agent preferably comprises at least one compound of the formula (I):

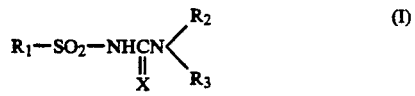

wherein X represents a member selected from the group consisting of oxygen and sulfur atoms, $R_1$ represents a member selected from the group consisting of unsubstituted aromatic cyclic hydrocarbon groups and substituted phenyl groups having at least one member selected from the group consisting of lower alkyl groups and halogen atoms, and $R_2$ and $R_3$ respectively and independently from each other represent a member selected from the group consisting of a hydrogen atom, alkyl groups, aryl groups, aralkyl groups, substituted alkyl groups having an aryloxy group, unsubstituted aromatic cyclic hydrocarbon groups, and substituted aromatic cyclic hydrocarbon groups having at least one member selected from the group consisting of alkyl groups, aryl groups, aralkyl groups, alkyloxy groups, alkyloxycarbonyl groups, aryloxycarbonyl groups, aralkyloxycarbonyl groups, arylsulfonyl groups and halogen atoms.

In the formula (I), the unsubstituted aromatic cyclic hydrocarbon groups standing for $R_1$ include phenyl, naphthyl and anthryl groups.

The lower alkyl groups contained as substituents in the substituted phenyl groups standing for $R_1$ preferably have 1 to 4 carbon atoms and preferably are selected from the group consisting of methyl, ethyl, propyl and butyl groups, and the halogen atoms are selected from F, Cl, Br and I. With respect to $R_2$ and $R_3$ in the formula (I), preferably, the alkyl groups have 1 to 8 carbon atoms and are selected from methyl, ethyl, propyl, butyl, pentyl, hexyl and octyl; the aryl groups are selected from phenyl, naphtyl and anthryl groups; the aralkyl groups are preferably selected from benzyl phenetyl and methyl benzyl groups; the aryloxy group-substituted alkyl groups are selected from phenoxy methyl, phenoxy ethyl and nathoxy ethyl groups; the unsubstituted aromatic cyclic hydrocarbon groups are selected from phenyl, naphthyl and anthryl groups; and the substituted aromatic cyclic hydrocarbon groups are selected from substituted phenyl, naphthyl and anthryl groups having at least one substituent as defined above.

With respect to the substituent of the substituted aromatic cyclic hydrocarbon groups standing for $R_2$ and $R_3$, preferably, the alkyl groups have 1 to 4 carbon atoms and are selected from methyl, ethyl, propyl and butyl groups; the aryl groups are selected from phenyl, and naphthyl groups; the aralkyl groups are selected from benzyl, phenetyl and methyl benzyl; alkyloxy groups are selected from methoxy, ethoxy, propoxy and butoxy groups; the alkyloxycarbonyl groups are selected from $CH_3OCO-$, $C_2H_5OCO-$, $C_3H_7OCO-$ and $C_4H_9OCO-$ groups; the aryloxycarbonyl groups are selected from $C_6H_5OCO-$, $CH_3-C_6H_5OCO-$, $CH_3O-C_6H_5OCO-$ and naphthyloxycarbonyl groups; the aralkyloxycarbonyl groups are selected from $C_6H_5CH_2OCO-$, $CH_3-C_6H_5CH_2OCO-$ and naphthylmethyloxycarbonyl groups; the arylsulfonyl groups are selected from $C_6H_5SO_2-$, $CH_3-CH_6H_5SO_2-$ and naphthylsulfonyl groups; and halogen atoms are selected from F, Cl, Br and I.

The color developing N-arylsulfonyl(thio)urea compound of the formula (I) is preferably selected from the group consisting of N-(p-toluenesulfonyl)-N'-phenylurea (m.p.: 165° C.), N-(p-toluenesulfonyl)-N'-(p-methoxyphenyl)urea (m.p.: 155° C.), N-(p-toluenesulfonyl)-N'-(o-tolyl)urea (m.p.: 148° C.), N-(p-toluenesulfonyl)-N'-(m-tolyl)urea (m.p.: 184° C.), N-(p-toluenesulfonyl)-N'-(p-tolyl)urea (m.p.: 149° C.), N-(p-toluenesulfonyl)-N'-(p-n-butylphenyl)urea, N-(p-toluenesulfonyl)-N',N'-diphenylurea (m.p.: 159° C.), N-(p-toluenesulfonyl)-N'-(o-chlorophenyl)urea (m.p.: 180° C.), N-(p-toluenesulfonyl)-N'-(m-chlorophenyl)urea (m.p.: 193° C.), N-(p-toluenesulfonyl)-N'-(2,4-dichlorophenyl)urea, N-(p-toluenesulfonyl)-N'-methyl-N'-phenylurea (m.p.: 155° C.), N-(p-toluenesulfonyl)-N'-benzylurea (m.p.: 177° C.), N-(p-toluenesulfonyl)-N'-(1-naphthyl)urea (m.p.: 124° C.), N-(p-toluenesulfonyl)-N'-[1-(2-methylnaphthyl)]urea, N-(benzenesulfonyl)-N'-phenylurea (m.p.: 153° C.), N-(p-chlorobenzenesulfonyl)-N'-phenylurea, N-(o-toluenesulfonyl)-N'-phenylurea, N-(p-toluenesulfonyl)-N'-methylurea (m.p.: 172° C.), N-(p-toluenesulfonyl)-N'-ethylurea (m.p.: 141° C.), N-(p-toluenesulfonyl)-N'-(2-phenoxyethyl)urea (m.p.: 191° C.), N,N'-bis(p-toluenesulfonyl)urea (m.p.: 155° C.), N-(p-toluenesulfonyl)-N'-phenylthiourea, N-(p-toluenesulfonyl)-N'-(o-diphenyl)urea, (m.p.: 148° C.), and N-(p-toluenesulfonyl)-N'-(p-ethoxycarbonylphenyl)urea.

The above-mentioned compounds of the formula (I) can be employed alone or as a mixture of two or more of those compounds.

Some of the N-arylsulfonyl(thio)urea compounds of the formula (I) are novel compounds. The compounds of the formula (I) can be prepared in accordance with the following reactions (1) to (4): Reaction (1):

Reaction (1):

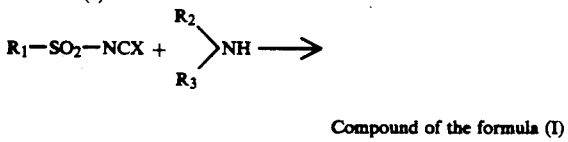

Compound of the formula (I)

Reaction (2):

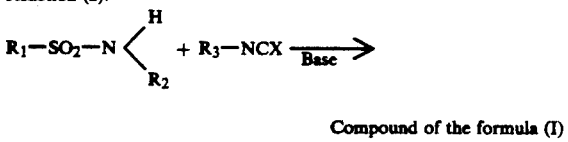

Compound of the formula (I)

Reaction (3):

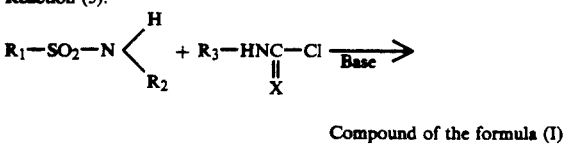

Compound of the formula (I)

Reaction (4):

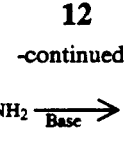

Compound of the formula (I)

In the above-mentioned formulae, $R_1$, $R_2$ and $R_3$ are as defined for the formula (I).

In the thermosensitive colored image-forming layer of the present invention, the color developing agent optionally contains at least one conventional color-developing compound in addition to the N-arylsulfonyl(thio)urea compound of the formula (I), to further enhance the color-forming performance of the colored image-forming layer.

The conventional color developing compound is preferably selected from the group consisting of 2,2-bis(4-hydroxyphenyl)propane (namely bisphenol A), 1,1-bis(4-hydroxyphenyl)-1-phenylethane, 1,4-bis[1-methyl-1-(4'-hydroxyphenyl)ethyl]benzene, 1,3-bis[1-methyl-1-(4'-hydroxyphenyl)ethyl]benzene, dihydroxydiphenylether (disclosed in JP-A-1-180,382), benzyl p-hydroxy-benzoate (disclosed in JP-A-52-140,483), bisphenol S, 4-hydroxy-4'-isopropyl-oxydiphenylsulfone (disclosed in JP-A-60-13,852), 1,1-di-(4-hydroxyphenyl)-cyclohexane, 1,7-di(4-hydroxyphenylthio)-3,5-dioxaheptane (disclosed in JP-A-59-52,694), and 3,3'-diallyl-4,4'-dihydroxydiphenylsulfone (disclosed in JP-A-60-208,286).

The above-mentioned conventional color developing compounds can be employed alone or as a mixture of two or more thereof.

The dye precursor usable for the present invention comprises at least one member selected from conventional triphenylmethane, fluoran and diphenylmethane leuco dyes, for example, 3-(4-diethylamino-2-ethoxyphenyl)-3-(1-ethyl-2-methylindole-3-il)-4-azaphthalide, crystal violet lactone, 3-(N-ethyl-N-isopentylamino)-6-methyl-7-anilinofluoran, 3-diethylamino-6-methyl-7-anilinofluoran, 3-diethylamino-6-methyl-7-(2', 4'-dimenthyl-anilino) fluoran, 3-(N-ethyl-N-p-toluidino)-6-methyl-7-anilinofluoran, 3-pyrrolidino-6-methyl-7-anilinofluoran, 3-dibutylamino-6-methyl-7-anilinofluoran, 3-(N-cyclohexyl-N-methylamino)-6-methyl-7-anilinofluoran, 3-diethylamino-7-(o-chloroanilino)fluoran, 3-diethylamino-7-(m-trifluoromethylanilino)fluoran, 3-diethylamino-6-methyl-7-chlorofluoran, 3-diethylamino-6-methylfluoran, 3-cyclohexylamino-6-chlorofluoran and 3-(N-ethyl-N-hexylamino)-6-methyl-7-(p-chloroanilino) fluoran.

The binder usable for the present invention preferably comprises at least one member selected from water-soluble polymeric materials, for example, various types of polyvinyl alcohol resins which have a different molecular weight from each other, starch and starch derivatives, cellulose derivatives, for example, methoxy cellulose, carboxymethyl cellulose, methyl cellulose and ethyl cellulose, sodium polyacrylate, polyvinyl pyrrolidine, acrylic acid amide-acrylic acid ester copolymers, acrylic acid amide-acrylic acid estermethacrylic acid terpolymers, alkali salts of styrenemaleic anhydride copolymers, polyacrylic acid amide, sodium alginate, gelatine and casein, and water-insoluble polymeric materials, for example, polyvinyl acetate resins, polyurethane resins, styrene-butadiene copolymer resins, polyacrylic acid resins, polyacrylic acid ester resins, vinyl chloride-vinyl acetate copolymer resins, polybutyl acrylate, ethylene-vinyl acetate copolymer resins and styrene-butadiene-acrylic compound-terpolymer resins, used in the form of a latex.

In the thermosensitive colored image-forming layer of the present invention, the dye precursor is present in an amount of 5 to 20% by weight, the color developing agent is present in an amount of 5 to 40% by weight, and the binder is present in an amount of 5 to 20% by weight, based on the total dry weight of the colored image-forming layer.

The color developing agent contains the N-arylsulfonyl(thio)urea compound of the formula (I) in an amount of 30% to 100% by weight and the conventional color developing compound in an amount of 0 to 70% by weight.

Also, in the thermosensitive colored image-forming layer, the colored image-stabilizing agent is present in an amount of 1 to 30% and the additional image-stabilizing agent is present in an amount of 1 to 30%, based on the total dry weight of the colored image-forming layer.

The thermosensitive colored image-forming layer of the present invention optionally further comprises a heat-fusible organic substance, usually referred to as a sensitizing agent, inorganic and organic pigments, antioxidants, for example, hindered phenol compounds, ultraviolet ray-absorbers, and waxes.

The sensitizing agent comprises at least one organic compound having a melting point of from 50° C. to 160° C., for example, phenyl 1-hydroxy-2-naphthoate (JP-A-57-191,089), p-benzyl-biphenyl (JP-A-60-82,382), benzylnaphthylether (JP-A-58-87,094), dibenzyl terephthalate (JP-A-58-98,285), benzyl p-benzyloxybenzoate (JP-A-57-201,691), diphenyl carbonate, ditolyl carbonate (JP-A-58-136,489), m-therphenyl (JP-A-57-89,994), 1,2-bis(m-tolyloxy)ethane (JP-A-60-56,588), 1,5-bis(p-methoxyphenoxy)-3-oxapentane (JP-A-62-181,183), oxalic acid diesters (JP-A-64-1,583) and 1,4-bis(p-tolyloxy) benzene (JP-A-2-153,783).

The inorganic and organic pigments usable for the present invention are preferably selected from inorganic fine particles of, for example, calcium carbonate, silica, zinc oxide, titanium dioxide, aluminum hydroxide, zinc hydroxide, barium sulfate, clay, anhydrous clay, talc, and surface-treated calcium carbonate and silica and organic fine particles of, for example, urea-formaldehyde resins, styrene-methacrylate copolymer resins and polystyrene resins.

The antioxidants and ultraviolet ray-absorbers are preferably selected from those disclosed in JP-A-57-151,394, JP-A-58-160,191, JP-A-58-69,096, JP-A-59-2,884, JP-A-59-95,190, JP-A-60-22,288, JP-A-60-255,485, JP-A-61-44,686, JP-A-62-169,683, JP-A-63-17,081 and JP-A-1-249,385, for example, 1,1,3-tris(3'-cycloxyl-4'-hydroxyphenyl)butane; 1,1,3-tris(2-methyl-4-hydroxy-5-tert-butylphenyl)butane, 4,4-thio-bis(3-methyl-6-tert-butylphenol), 1,3,5-trimethyl-2,4,6-tris(3,5-di-tertbutyl-4-hydroxybenzyl)benzene, 2,2'-dihydroxy-4,4'-dimethoxybenzophenone, p-octylphenyl salycilate, 2-(2'-hydroxy-5'-methylphenyl)benzotriazole, ethyl-2-cyano-3, 3'-diphenyl acrylate, and tetra(2,2,6,6-tetramethyl-4-piperidyl)-1,2,3,4-butane-tetracarbonate.

The waxes usable for the present invention preferably comprise at least one member selected from, for example, paraffin waxes, carnauba wax, microcrystalline waxes, polyethylene waxes, amide type waxes, bisimide type waxes, higher fatty acid amide waxes, for example, stearic acid amide, ethylene-bis-stearoamide wax, higher fatty acid esters and metal salts, for example, zinc stearate, aluminum stearate calcium stearate and zinc oleate.

In the colored image-forming layer of the present invention, the sensitizing agent is preferably contained in an amount of 5 to 40% by weight, the wax and organic or inorganic pigment are optionally contained in amounts of 2 to 20% by weight and 5 to 50% by weight, respectively, and the antioxidant and ultraviolet ray-absorber are contained preferably in an amount of 1 to 10%, based on the total dry weight of the colored image-forming layer.

The sheet substrate usable for the present invention is not limited to a specific group of materials, and usually the sheet substrate comprises a member selected from fine paper sheets, coated paper sheet having a clay or latex-coated layer, cast-coated paper sheets, paper boards, plastic resin films, synthetic paper sheets comprising a plastic resin such as a polyolefin resin and a multi-layer structure, and laminated composite sheets. Preferably, the sheet substrate has a basis weight of 40 to 170 g/m².

The colored image-forming layer can be formed on a surface of a sheet substrate, by applying a coating liquid containing the above-mentioned components, and by drying and solidifying the coating liquid layer on the sheet substrate.

The colored image-forming layer is preferably present in a dry weight of from 1 to 15 g/m², more preferably 2 to 10 g/m².

In the present thermosensitive recording material, a protective layer and/or a printed layer may be formed on the colored image-forming layer.

In the thermosensitive colored image-forming layer of the present invention, the combination of the specific colored image-stabilizing agent comprising the aziridinyl compound and/or the epoxy compound with the specific additional colored image-stabilizing agent comprising the amino compound and the carboxylic compound significantly enhances the resistance of the resultant colored images to the oily and fatty substances and to the plasticizer, even immediately after the formation of the colored images.

Accordingly, the thermosensitive recording material of the present invention has an excellent storage persistency of the resultant colored images, and a satisfactory suitability for a high speed recording machine. Therefore the thermosensitive recording material of the present invention has a fully balanced quality and is very variable for practical use.

EXAMPLES

The present invention will be further explained by the following specific examples, which are merely representative and do not in any way restrict the scope of the present invention.

EXAMPLE 1

A thermosensitive recording paper sheet was prepared by the following procedures.

| (1) Preparation of an aqueous dye precursor dispersion A in the following composition | |
|---|---|
| Component | Part by weight |
| 3-(N-isopentyl-N-ethylamino)-6-methyl-7-anilinofluoran | 20 |

-continued

(1) Preparation of an aqueous dye precursor dispersion A in the following composition

| Component | Part by weight |
|---|---|
| 10% aqueous solution of polyvinyl alcohol | 10 |
| Water | 70 |

The composition was dispersed in a sand grinder to an extent such that the resultant dispersed solid particles had an average size of 1 μm or less.

(2) Preparation of an aqueous color-developing agent dispersion B in the following composition

| Component | Part by weight |
|---|---|
| 2,2-bis(4-hydroxyphenyl)propane (Bisphenol A) | 20 |
| 10% aqueous solution of polyvinyl alcohol | 10 |
| Water | 70 |

The composition was dispersed in a sand grinder to an extent such that the resultant dispersed solid particles had an average size of 1 μm or less.

(3) Preparation of an aqueous colored image-stabilizing agent dispersion C in the following composition

| Component | Part by weight |
|---|---|
| Bis[4-(1-aziridinylcarbonyl-amino)phenyl]methane | 20 |
| 10% aqueous solution of polyvinyl alcohol | 10 |
| Water | 70 |

The composition was dispersed in a sand grinder to an extent such that the resultant dispersed solid particles had an average size of 1 μm or less.

(4) Preparation of an aqueous additional colored image-stabilizing agent dispersion D in the following composition

| Component | Part by weight |
|---|---|
| Amino compound of the formula 18) | 20 |
| 10% aqueous solution of polyvinyl alcohol | 10 |
| Water | 70 |

The composition was dispersed in a sand grinder to an extent such that the resultant dispersed solid particles had an average size of 1 μm or less.

(5) Preparation of a Pigment-Coated Paper Sheet

A coating liquid was prepared by mixing an aqueous dispersion, prepared by dispersing 85 parts by weight of anhydrous clay available under the trademark of Ansilex, from Engelhard Corporation, in 320 parts by weight of water, with 40 parts by weight of an aqueous emulsion of a styrene-butadiene copolymer in a solid concentration of 50% by weight and 50 parts by weight of a 10% aqueous oxidized starch solution.

The coating liquid was coated on a surface of a fine paper sheet having a basis weight of 48 g/m², to form a coating layer having a dry weight of 7.0 g/m², whereby coated paper sheet was obtained.

(6) Formation of Thermosensitive Colored Image-Forming Layer

A coating liquid was prepared by evenly mixing 50 parts by weight of the aqueous dye precursor dispersion A, 50 parts by weight of the aqueous color-developing agent dispersion B, 100 parts by weight of the aqueous aziridinyl compound dispersion C and 50 parts by weight of the aqueous amino compound dispersion D, with 30 parts by weight of an anhydrous clay, 20 parts by weight of a 25% aqueous zinc stearate dispersion, 15 parts by weight of 30% aqueous paraffin dispersion, and 120 parts by weight of a 10% aqueous polyvinyl alcohol solution, by agitating the mixture.

A surface of the pigment coated paper sheet was coated with the resultant coating liquid and dried. A thermosensitive colored image-forming layer was formed in a weight of 5.0 g/m², to provide a thermosensitive recording paper sheet.

The recording sheet was treated by a super calender, and the calendered surface of the recording sheet had a Bekk smoothness of 600 to 1000 seconds.

A specimen of the resultant thermosensitive recording sheet was subjected to a colored image-developing test in 64 lines by using a dynamic color-developing tester provided by modifying a thermosensitive facsimile printer, at an one line recording time of 10 m sec., at a scanning line density of 8×8 dot/mm, and with an applied energy of 0.54 mj/dot. The resultant black colored images were clear and had a high color density of 1.0 or more determined by Macbeth Reflection Color Density Tester RD-914 (trademarks).

The color image-developed specimen was subjected within 30 minutes from the completion of the color image-developing procedure, to a salad oil resistance test in such a manner that a salad oil was applied to the color image-developed surface of the specimen by using a cotton applicator, the salad oil-applied specimen was left to stand at room temperature for 30 minutes, and thereafter, the remaining colored images were evaluated by a naked eye observation.

The results of the above-mentioned tests are shown in Table 1.

EXAMPLE 2

A thermosensitive recording paper sheet was prepared by the same procedures as in Example 1 except that, in the preparation of the aqueous dispersion D, the amino compound of the formula 18) was replaced by the amino compound of the formula 20).

The test results are shown in Table 1.

EXAMPLE 3

A thermosensitive recording paper sheet was prepared by the same procedures as in Example 1 except that, in the preparation of the aqueous dispersion D, the amino compound of the formula 18) was replaced by the —CO—O—CO— group-containing compound of the formula 28).

The test results are shown in Table 1.

EXAMPLE 4

A thermosensitive recording paper sheet was prepared by the same procedures as in Example 1 except that, in the preparation of the aqueous dispersion D, the amino compound of the formula 18) was replaced by the carboxylic compound of the formula 33).

The test results are shown in Table 1.

EXAMPLE 5

A thermosensitive recording paper sheet was prepared by the same procedures as in Example 1 except that, in the preparation of the aqueous dispersion C, the bis[4-(1-aziridinylcarbonylamino)phenyl]methane was replaced by 2,4-bis(1-aziridinylcarbonylamino)toluene.

The test results are shown in Table 1.

EXAMPLE 6

A thermosensitive recording paper sheet was prepared by the same procedures as in Example 1 except that, in the preparation of the aqueous dispersion B, the bisphenol A was replaced by benzyl p-hydroxybenzoate.

The test results are shown in Table 1.

EXAMPLE 7

A thermosensitive recording paper sheet was prepared by the same procedures as in Example 1 except that, in the preparation of the aqueous dispersion B, the bisphenol A was replaced by 1,1-bis(4-hydroxyphenyl)-phenylethane.

The test results are shown in Table 1.

COMPARATIVE EXAMPLE 1

A thermosensitive recording paper sheet was prepared by the same procedures as in Example 1 except that, in the preparation of the coating liquid for the thermosensitive colored, image-forming layer, the aqueous dispersion A was used in an amount of 80 parts by weight, the aqueous dispersion B was employed in an amount of 160 parts by weight, and the aqueous dispersions C and D were not used.

The test results are shown in Table 1.

COMPARATIVE EXAMPLE 2

A thermosensitive recording paper sheet was prepared by the same procedures as in Example 1 except that, in the preparation of the coating liquid for the thermosensitive, colored image-forming layer, the aqueous dispersion B was employed in an amount of 100 parts by weight, and the aqueous dispersion D was not used.

The test results are shown in Table 1.

COMPARATIVE EXAMPLE 3

A thermosensitive recording paper sheet was prepared by the same procedures as in Comparative Example 2 except that, in the preparation of the aqueous dispersion B, the bisphenol A was replaced by benzyl p-hydroxybenzoate.

The test results are shown in Table 1.

COMPARATIVE EXAMPLE 4

A thermosensitive recording paper sheet was prepared by the same procedures as in Comparative Example 2 except that, in the preparation of the aqueous dispersion B, the bisphenol A was replaced by 1,1-bis(4-hydroxyphenyl)-1-phenylethane.

The test results are shown in Table 1.

TABLE 1

| Example No. | Item | Resistance of colored images to salad oil[*1] |
|---|---|---|
| Example | 1 | 3 |
|  | 2 | 3 |
|  | 3 | 3 |
|  | 4 | 3 |
|  | 5 | 3 |
|  | 6 | 3 |
|  | 7 | 3 |
| Comparative Example | 1 | 1 |
|  | 2 | 2 |
|  | 3 | 2 |
|  | 4 | 2 |

Note:
[*1] ... 3 ... Remaining colored images were clear.
2 ... Remaining colored images were slightly faded.
1 ... No colored images remained.

EXAMPLE 8

A thermosensitive recording paper sheet was prepared by the same procedures as in Example 1 except that, in the preparation of the aqueous dispersion C, the bis[4-(1-aziridinylcarbonylamino)phenyl]methane was replaced by the epoxy compound of the formula 1).

The test results are shown in Table 2.

EXAMPLE 9

A thermosensitive recording paper sheet was prepared by the same procedures as in Example 8 except that, in the preparation of the aqueous dispersion D, the amino compound of the formula 18) was replaced by the amino compound of the formula 20).

The test results are shown in Table 2.

EXAMPLE 10

A thermosensitive recording paper sheet was prepared by the same procedures as in Example 8 except that, in the preparation of the aqueous dispersion D, the amino compound of the formula 18) was replaced by the —CO—O—CO— group-containing compound of the formula 28).

The test results are shown in Table 2.

EXAMPLE 11

A thermosensitive recording paper sheet was prepared by the same procedures as in Example 8 except that, in the preparation of the aqueous dispersion D, the amino compound of the formula 18) was replaced by the carboxyl compound of the formula 33).

The test results are shown in Table 2.

EXAMPLE 12

A thermosensitive recording paper sheet was prepared by the same procedures as in Example 8 except that, in the preparation of the aqueous dispersion C, the epoxy compound of the formula 1) was replaced by the epoxy compound of the formula 2).

The test results are shown in Table 2.

EXAMPLE 13

A thermosensitive recording paper sheet was prepared by the same procedures as in Example 8 except that, in the preparation of the aqueous dispersion B, the bisphenol A was replaced by the benzyl p-hydroxybenzoate.

The test results are shown in Table 2.

EXAMPLE 14

A thermosensitive recording paper sheet was prepared by the same procedures as in Example 8 except that, in the preparation of the aqueous dispersion B, the bisphenol A was replaced by 1,1-bis(4-hydroxyphenyl)-1-phenylethane.

The test results are shown in Table 2.

COMPARATIVE EXAMPLE 5

A thermosensitive recording paper sheet was prepared by the same procedures as in Example 8 except that, in the preparation of the coating liquid for the thermosensitive colored image-forming layer, the aqueous dispersion B was used in an amount of 100 parts by weight, and the aqueous dispersion D was not used.

The test results are shown in Table 2.

COMPARATIVE EXAMPLE 6

A thermosensitive recording paper sheet was prepared by the same procedures as in Comparative Example 5 except that, in the preparation of the aqueous dispersion B, the bisphenol A was replaced by benzyl p-hydroxybenzoate.

The test results are shown in Table 2.

COMPARATIVE EXAMPLE 7

A thermosensitive recording paper sheet was prepared by the same procedures as in Comparative Example 5 except that, in the preparation of the aqueous dispersion B, the bisphenol A was replaced by 1,1-bis(4-hydroxyphenyl)-1-phenylethane.

The test results are shown in Table 2.

TABLE 2

| Example No. | Item | Resistance of colored images to salad oil*1 |
|---|---|---|
| Example | 8 | 3 |
|  | 9 | 3 |
|  | 10 | 3 |
|  | 11 | 3 |
|  | 12 | 3 |
|  | 13 | 3 |
|  | 14 | 3 |
| Comparative | 5 | 2 |
| Example | 6 | 2 |
|  | 7 | 2 |

Note:
*1... 3 ... Remaining colored images were clear.
2 ... Remaining colored images were slightly faded.
1 ... No colored images remained.

EXAMPLE 15

A thermosensitive recording paper sheet was prepared by the following procedures.

(1) Preparation of an aqueous dye precursor dispersion A in the following composition

| Component | Part by weight |
|---|---|
| 3-(N-isopentyl-N-ethylamino)-6-methyl-7-anilinofluoran | 20 |
| 10% aqueous solution of polyvinyl alcohol | 10 |
| Water | 70 |

The composition was dispersed in a sand grinder to an extent such that the resultant dispersed solid particles had an average size of 1 μm or less.

(2) Preparation of an aqueous color-developing agent dispersion B in the following composition

| Component | Part by weight |
|---|---|
| N-(p-toluenesulfonyl)-N'- | 20 |

-continued (2) Preparation of an aqueous color-developing agent dispersion B in the following composition

| Component | Part by weight |
|---|---|
| phenylurea |  |
| 10% aqueous solution of polyvinyl alcohol | 10 |
| Water | 70 |

The composition was dispersed in a sand grinder to an extent such that the resultant dispersed solid particles had an average size of 1 μm or less.

(3) Preparation of an aqueous colored image-stabilizing agent dispersion C in the following composition

| Component | Part by weight |
|---|---|
| Bis[4-(1-aziridinylcarbonylamino)phenylmethane | 20 |
| 10% aqueous solution of polyvinyl alcohol | 10 |
| Water | 70 |

The composition was dispersed in a sand grinder to an extent such that the resultant dispersed solid particles had an average size of 1 μm or less.

(4) Preparation of an aqueous additional colored image-stabilizing agent dispersion D in the following composition

| Component | Part by weight |
|---|---|
| Carboxylic compound of the formula 37) | 20 |
| 10% aqueous solution of polyvinyl alcohol | 10 |
| Water | 70 |

The composition was dispersed in a sand grinder to an extent such that the resultant dispersed solid particles had an average size of 1 μm or less.

(5) Preparation of an aqueous sensitizing agent dispersion E in the following composition

| Component | Part by weight |
|---|---|
| Di-p-methylbenzyl oxalate | 20 |
| 10% aqueous solution of polyvinyl alcohol | 10 |
| Water | 70 |

The composition was dispersed in a sand grinder to an extent such that the resultant dispersed solid particles had an average size of 1 μm or less.

(6) Preparation of a Pigment-Coated Paper Sheet

A coating liquid was prepared by mixing an aqueous dispersion, prepared by dispersing 85 parts by weight of anhydrous clay available under the trademark of Ansilex, from Engelhard Corporation, in 320 parts by weight of water, with 40 parts by weight of an aqueous emulsion of a styrene-butadiene copolymer in a solid concentration of 50% by weight and 50 parts by weight of a 10% aqueous oxidized starch solution.

The coating liquid was coated on a surface of a fine paper sheet having a basis weight of 48 g/m², to form a coating layer having a dry weight of 7.0 g/m², whereby coated paper sheet was obtained.

(7) Formation of Thermosensitive Colored Image-Forming Layer

A coating liquid was prepared by evenly mixing 50 parts by weight of the aqueous dye precursor dispersion A, 100 parts by weight of the aqueous color-developing agent dispersion B, 40 parts by weight of the aqueous aziridinyl compound dispersion C, 10 parts by weight of the aqueous carboxylic compound dispersion D, and 75 parts by weight of the aqueous sensitizing agent dispersion E, with 27 parts by weight of an anhydrous clay, 25 parts by weight of a 25% aqueous zinc stearate dispersion, 30 parts by weight of a 30% aqueous paraffin dispersion, and 100 parts by weight of a 10% aqueous polyvinyl alcohol solution, by agitating the mixture.

A surface of the pigment coated paper sheet was coated with the resultant coating liquid and dried. A thermosensitive colored image-forming layer was formed in a weight of 5.0 g/m$^2$, to provide a thermosensitive recording paper sheet.

The recording sheet was treated by a super calender, and the calendered surface of the recording sheet had a Bekk smoothness of 600 to 1000 seconds.

A specimen of the resultant thermosensitive recording sheet was subjected to the same colored image-developing test in 64 lines as in Example 1. The resultant black colored images were clear and had a high color density of 1.2 or more determined by Macbeth Reflection Color Density Tester RD-914 (trademark).

The color image-developed specimen was subjected to the same salad oil resistance test as in Example 1. Further, the color image-developing specimen was subjected to a plasticizer resistance test in the same manner as in the salad oil resistance test, except that the salad oil was replaced by dioctyl phthalate.

In each of the salad oil and plasticizer tests, the remaining colored images were evaluated by a naked eye observation.

The results of the above-mentioned tests are shown in Table 3.

EXAMPLE 16

A thermosensitive recording paper sheet was prepared by the same procedures as in Example 15 except that, in the preparation of the aqueous dispersion D, the carboxylic compound of the formula 37) was replaced by the carboxylic compound of the formula 36).

The test results are shown in Table 3.

EXAMPLE 17

A thermosensitive recording paper sheet was prepared by the same procedures as in Example 15 except that, in the preparation of the aqueous dispersion B, the N-(p-toluenesulfonyl)-N'-phenylurea was replaced by N-(p-toluenesulfonyl)-N'-(p-tolyl)urea, in the preparation of the aqueous dispersion C, the bis[4-(1-aziridinylcarbonylamino)phenyl]methane was replaced by the epoxy compound of the formula 1), and in the preparation of the aqueous dispersion D, the carboxylic compound of the formula 37) was replaced by the carboxylic compound of the formula 33).

The test results are shown in Table 3.

EXAMPLE 18

A thermosensitive recording paper sheet was prepared by the same procedures as in Example 15 except that, in the preparation of the aqueous dispersion B, the N-(p-toluenesulfonyl)-N'-phenylurea was replaced by N-(p-toluenesulfonyl)-N'-(p-tolyl)urea, and in the preparation of the aqueous dispersion D, the carboxylic compound was replaced by the primary amine compound of the formula 19).

The test results are shown in Table 3.

EXAMPLE 19

A thermosensitive recording paper sheet was prepared by the same procedures as in Example 15 except that, in the preparation of the aqueous dispersion C, the bis[4-(1-aziridinylcarbonylamino)phenyl]methane was replaced by 2,4-bis(1-aziridinylcarbonylamino)toluene, and in the preparation of the aqueous dispersion D, the carboxylic compound of the formula 37) was replaced by the secondary amine compound of the formula 22).

The test results are shown in Table 3.

EXAMPLE 20

A thermosensitive recording paper sheet was prepared by the same procedures as in Example 15 except that, in the preparation of the aqueous dispersion D, the carboxylic compound of the formula 37) was replaced by the carboxylic anhydride compound of the formula 28.

The test results are shown in Table 3.

COMPARATIVE EXAMPLE 8

A thermosensitive recording paper sheet was prepared by the same procedures as in Example 15 except that, in the preparation of the aqueous dispersion B, the N-(p-toluenesulfonyl)-N'-phenylurea was replaced by 2,2-bis(4-hydroxyphenyl)propane, namely bisphenol A, and in the preparation of the coating liquid for the thermosensitive colored image-forming layer, the aqueous dispersion A was used in an amount of 65 parts by weight, the dispersion B was used in an amount of 105 parts by weight, the dispersion E was used in an amount of 105 parts by weight and the aqueous dispersions C and D were omitted.

The test results are shown in Table 3.

COMPARATIVE EXAMPLE 9

A thermosensitive recording paper sheet was prepared by the same procedures as in Example 15 except that, in the preparation of the aqueous dispersion B, the N-(p-toluenesulfonyl)-N'-phenylurea was replaced by 2,2-bis(4-hydroxyphenyl)propane, namely bisphenol A, and in the preparation of the coating liquid for the thermosensitive colored image-forming layer, the aqueous dispersion D was omitted.

The test results are shown in Table 3.

COMPARATIVE EXAMPLE 10

A thermosensitive recording paper sheet was prepared by the same procedures as in Example 15 except that, in the preparation of the aqueous dispersion B, the N-(p-toluenesulfonyl)-N'-phenylurea was replaced by N-(p-toluenesulfonyl)-N'-(p-tolyl)urea, and in the preparation of the coating liquid for the thermosensitive formula 20) colored image-forming layer, the aqueous dispersion D was omitted.

The test results are shown in Table 3.

TABLE 3

| Example Nos. | Items | Resistance of colored images to salad oil[*2] | Resistance of colored images to dioctyl phthalate (plasticizer)[*2] |
|---|---|---|---|
| Example | 15 | 4 | 4 |
|  | 16 | 4 | 4 |
|  | 17 | 4 | 3 |
|  | 18 | 4 | 4 |
|  | 19 | 4 | 4 |
|  | 20 | 4 | 4 |
| Comparative Example | 8 | 1 | 1 |
|  | 9 | 2 | 1 |
|  | 10 | 3 | 3 |

Note:
[*2] 4 ... Remaining color images were clear.
3 ... Remaining color images were readable.
2 ... Remaining color images were faded and dim.
1 ... Colored images were completely faded.

We claim:

1. A thermosensitive recording material comprising:
a sheet substrate; and
a thermosensitive image-forming layer formed on a surface of the sheet substrate and comprising a substantially colorless dye precursor, a color developing agent reactive with the dye precursor upon heating to thereby develop a color, a colored image-stabilizing agent comprising at least one member selected from the group consisting of aromatic aziridinyl compounds having at least one aziridinyl group, and aromatic epoxy compounds having at least one epoxy group, and a binder,
said thermosensitive colored image-forming layer further containing an additional colored image-stabilizing agent comprising a member selected from the group consisting of (1) amino compounds having at least one member selected from the group consisting of primary and secondary amine groups, (2) mixtures of at least two of the amino compounds, (3) carboxylic compounds having at least one member selected from the group consisting of a carboxyl group and a group of the formula —CO—O—CO—, and (4) mixtures of at least two of the carboxyl compounds, the amino compounds being selected from the group consisting of the compounds of the formulae:

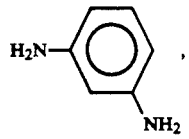

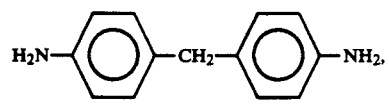

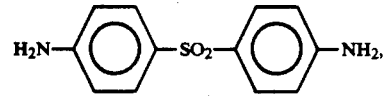

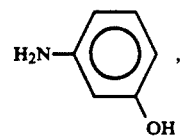

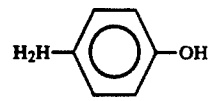

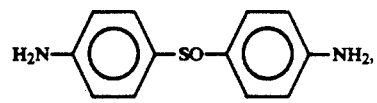

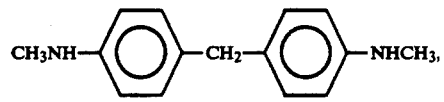

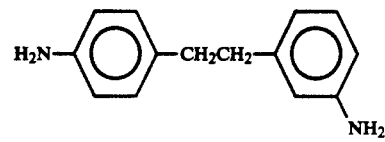

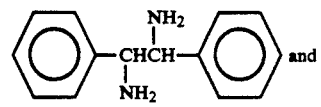

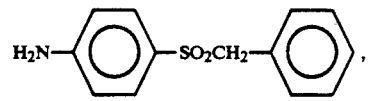

and the carboxylic compounds being selected from the group consisting of the compounds of the formulae:

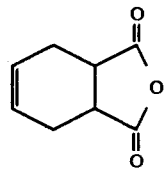

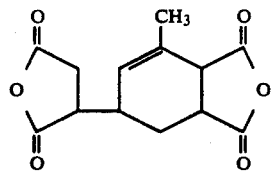

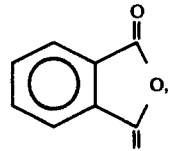

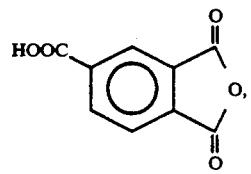

-continued

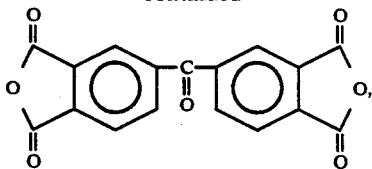

HOOC(CH$_2$)$_4$COOH,

HOOC(CH$_2$)$_2$COOH,

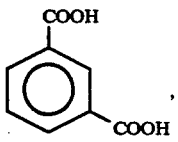

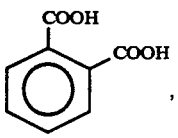

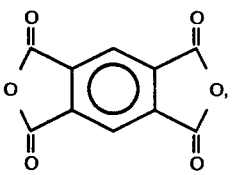

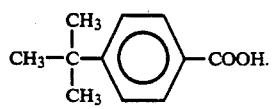

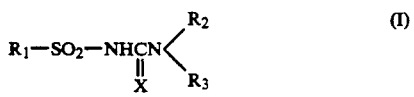

2. The thermosensitive recording material as claimed in claim 1, wherein the color developing agent comprises at least one compound of the formula (I):

$$R_1-SO_2-NHC{\overset{R_2}{\underset{R_3}{\diagup}}}\atop{\underset{X}{\|}}\qquad(I)$$

wherein X represents a member selected from the group consisting of oxygen and sulfur, R$_1$ represents a member selected from the group consisting of unsubstituted aromatic cyclic hydrocarbon group and substituted phenyl group having at least one member selected from the group consisting of lower alkyl group and halogen, and R$_2$ and R$_3$ respectively and independently from each other represent a member selected from the group consisting of a hydrogen atom, alkyl group, aryl group, aralkyl group, substituted alkyl group having an aryloxy group, unsubstituted aromatic cyclic hydrocarbon group and substituted aromatic cyclic hydrocarbon group having at least one member selected from the group consisting of alkyl group, aryl group, aralkyl group, alkyloxy group, alkyloxycarbonyl group, aryloxycarbonyl group, aralkyloxycarbonyl group, arylsulfonyl group and halogen.

3. The thermosensitive recording material as claimed in claim 2, wherein the compound of the formula (I) for the color developing agent is selected from the group consisting of N-(p-toluenesulfonyl)-N'-phenylurea, N-(p-toluenesulfonyl)-N'-(p-methoxyphenyl)urea, N-(p-toluenesulfonyl)-N'-(o-tolyl)urea, N-(p-toluenesulfonyl)-N'-(m-tolyl)urea, N-(p-toluenesulfonyl)-N'-(p-tolyl)urea, N-(p-toluenesulfonyl)-N'-(p-n-butylphenyl)urea, N-(p-toluenesulfonyl)-N',N'-diphenylurea, N-(p-toluenesulfonyl)-N'-(o-chlorophenyl)urea, N-(p-toluenesulfonyl)-N'-(m-chlorophenyl)urea, N-(p-toluenesulfonyl)-N'-(2,4-dichlorophenyl)urea, N-(p-toluenesulfonyl)-N'-methyl-N'-phenyl urea, N-(p-toluenesulfonyl)-N'-benzylurea, N-(p-toluenesulfonyl)-N'-(1-naphthyl)urea, N-(p-toluenesulfonyl)-N'-[1-(2-methylnaphthyl)]urea, N-(benzenesulfonyl)-N'-phenylurea, N-(p-chlorobenzenesulfonyl)-N'-phenylurea, N-(o-toluenesulfonyl)-N'-phenylurea, N-(p-toluenesulfonyl)-N'-methylurea, N-(p-toluenesulfonyl)-N'-ethylurea, N-(p-toluenesulfonyl)-N'-(2-phenoxyethyl)urea, N,N'-bis(p-toluenesulfonyl)urea, N-(p-toluenesulfonyl)-N'-phenylthiourea, N-(p-toluenesulfonyl)-N'-(o-diphenyl)urea, and N-(p-toluenesulfonyl)-N'-(p-ethoxycarbonyl-phenyl)urea.

4. The thermosensitive recording material as claimed in claim 2, wherein the color developing agent is present in an amount of 5 to 40% based on the total dry weight of the thermosensitive colored image-forming layer.

5. The thermosensitive recording material as claimed in claim 1, wherein the aromatic aziridinyl compound for the colored image-stabilizing agent is selected from the group consisting of 2,4-bis(1-aziridinyl-carbonylamino)toluene, bis[4-(1-aziridinylcarbonylamino)phenyl]methane, bis[3-chloro-4-(1-aziridinylcarbonylamino)phenyl]methane, 2,2-bis[4-(1-aziridinylcarbonyloxy)phenyl]propane, 1,4-bis(1-aziridinylcarbonyl)benzene.

6. The thermosensitive recording material as claimed in claim 1, wherein the colored image-stabilizing agent comprises an aromatic epoxy compound selected from the group consisting of the compounds of formulae 1) to 15):

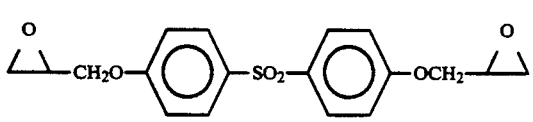

1)

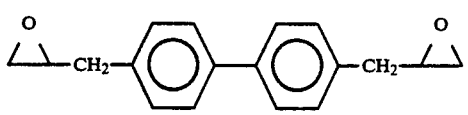

2)

-continued
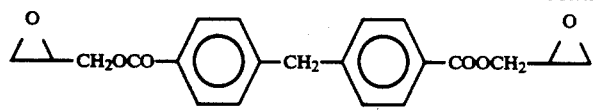  3)
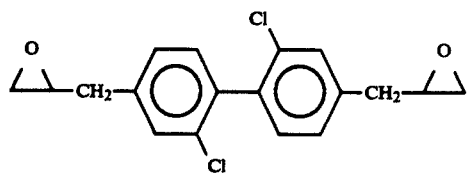  4)
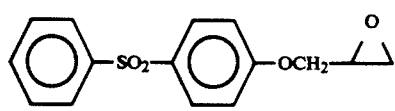  5)
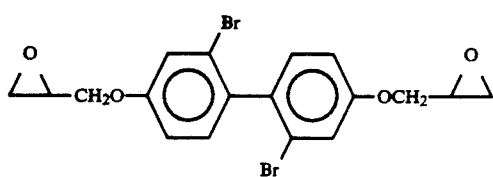  6)
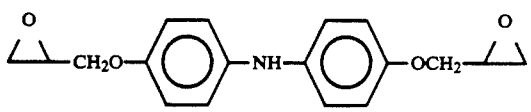  7)
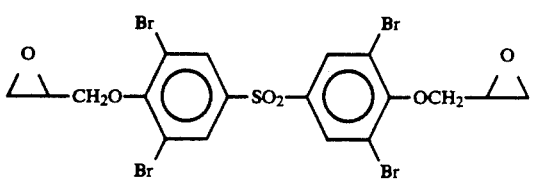  8)
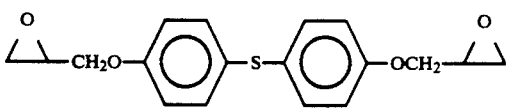  9)
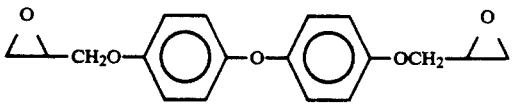  10)
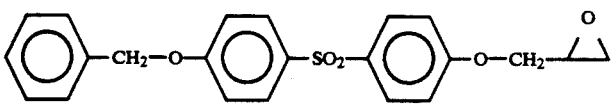  11)
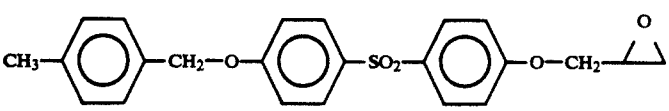  12)
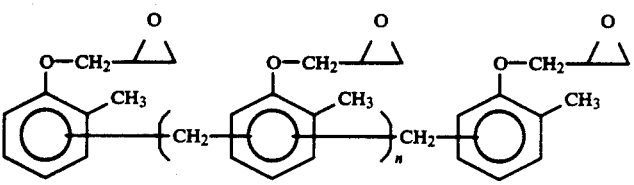  13)
in which formula 13, n represents an integer of 1 to 10, 14) 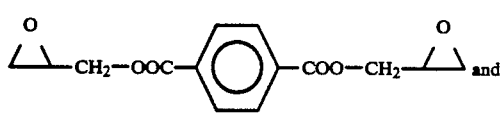

15) 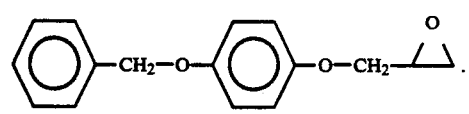

7. The thermosensitive recording material as claimed in claim 1, wherein the colored image-stabilizing agent is present in an amount of 1 to 30% based on the total dry weight of the thermosensitive colored image-forming layer.

8. The thermosensitive recording material as claimed in claim 1, wherein the additional colored image-stabilizing agent is present in an amount of 1 to 30% based on the total dry weight of the thermosensitive colored image-forming layer.

* * * * *